US005885963A

United States Patent [19]
Stockhoff et al.

[11] Patent Number: 5,885,963
[45] Date of Patent: Mar. 23, 1999

[54] CONTROLLING HEMIPTERAN INSECT PESTS WITH *BACILLUS THURINGIENSIS* ISOLATE PS123D1

[75] Inventors: Brian Stockhoff; Christopher Conlan, both of San Diego, Calif.

[73] Assignee: Mycogen Corporation, San Diego, Calif.

[21] Appl. No.: 657,579

[22] Filed: Jun. 7, 1996

Related U.S. Application Data

[63] Continuation-in-part of Ser. No. 475,924, Jun. 7, 1995, Pat. No. 5,723,440.

[51] Int. Cl.$^6$ .............................. A01N 63/02; A61K 38/16
[52] U.S. Cl. ........................................ 514/12; 424/93.461
[58] Field of Search ......................... 514/12; 424/93.461; 435/252.5

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herrnstadt et al. | 424/84 |
| 4,849,217 | 7/1989 | Soares et al. | 424/93 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 5,151,363 | 9/1992 | Payne | 435/252.5 |
| 5,273,746 | 12/1993 | Payne et al. | 424/93 |
| 5,298,245 | 3/1994 | Payne et al. | 424/93 |
| 5,302,387 | 4/1994 | Payne et al. | 424/93 |
| 5,508,032 | 4/1996 | Schnepf et al. | 424/93.462 |

FOREIGN PATENT DOCUMENTS

| | | |
|---|---|---|
| 0409438 | 1/1991 | European Pat. Off. . |
| 409 438 | 1/1991 | European Pat. Off. . |
| 931464 | 8/1993 | WIPO . |
| WO 95/02694 | 1/1995 | WIPO . |

OTHER PUBLICATIONS

Schnepf HE. "*Bacillus thruringiensis* toxins: regulation, activities and structural diversity." Curr. Opinions Biotech. 6: 305–312, 1995.

Beegle, C.C. (1978) "Use of Entomogenous Bacteria in Agroecosystems" Developments in Industrial Microbiologu 20:97–104.

Couch, T.L. (1980) "Mosquito Pathogenicity of *Bacillus thuringiensis* var. *israelensis*" Developments in Industrial Microbiology 22:61–76.

Feitelson, J.S. et al. (1992) "*Bacillus thuringiensis*: Insects and Beyond" Bio/Technology 10:271–275.

Gaerthner, F.H. (1989) "Cellular Delivery Systems for Insecticidal Proteins: Living and Non–Living Microorganisms" Controlled Delivery of Crop–Protection Agents, pp. 245–257.

Gaertner, F., L. Kim (1988) "Current Applied Recombinant DNA Projects"TIBTECH 6(4):S4–S7.

Hofte, H., H.R. Whiteley (1989) "Insecticidal Crystal Proteins of *Bacillus thuringiensis*" Microbiological Reviews 53(2):242–255.

Krieg, V.A. et al. (1983) "*Bacillus thuringiensis* var. *tenebrionis*: A New Pathotype Effective Against Larvae of Coleoptera" Z. ang. Ent. 96:500–508.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Jaquet, F. et al., (1987) "Specificity of *Bacillus thuringiensis* Delta–Endotoxin" Applied and Environmental Microbiology 53(3):500–504.

Prefontaine, G. et al. (1987) "Use of Oligonucleotide Probes to Study the Relatedness of Delta–Endotoxin Genes among *Bacillus thuringiensis* Subspecies and Strains" Applied and Environmental Microbiology 53(12):2808–2814.

Lambert, B. et al. (1992) "Novel *Bacillus thuringiensis* Insecticidal Cystal Protein with a Silent Activity against Coleopteran Larvae" Applied and Environmental Microbiology 58(8):2536–2542.

Cheung, P.Y.K. et al. (1985) "The Apparent in vivo Neuromuscular Effects to the δ–Endotoxin of *Bacillus thuringiensis* var. *isrealensis* in Mice and Insects of Four Orders" Pesticide Biochemistry and Physiology 23:85–94.1.

Tanigoshi, L.K. et al. (1990) "Efficacy of the β–Exotoxin of *Bacillus thuringiensis* to *Lygus hesperus* (Heteroptera: Miridae): Laboratory and Field Responses" Journal of Economic Entomology 83(6):2200–2206.

Farrag, R.M., F.N. Nasr (1992) "Efficacy of Chemical, Microbial Insecticides and Their Combinations Against the Cotton Seed Bug, *Oxycarenus hyalinipennis* Costs (Hemiptera:Lygaeidae)" Alex . Sci. Exch. 13(3):593–605.

Lima, M.M. et al. (1994) "Effects of the Spore–Endotoxin Complex of a Strain of *Bacillus thuringiensis* Serovar *morrisoni* upon *Triatoma vitticeps* (Hemiptera: Reduviidae) under Laboratory Conditions" Mem. Inst. Oswaldo Cruz 89(3):403–405.

*Primary Examiner*—Douglas W. Robinson
*Assistant Examiner*—Amy J. Nelson
*Attorney, Agent, or Firm*—Saliwanchik, Lloyd & Saliwanchik

[57] ABSTRACT

The subject invention concerns the use of *Bacillus thuringiensis* (*B.t.*) endotoxins to control hemipteran insect pests. Specifically exemplified is *B.t.* isolate PS123D1, and δ-endotoxins therefrom. These isolates and toxins can be administered to said pests, or to the environment of said pests, e.g. plants, to achieve control of the pests.

4 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 795 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: neoleoensis
        ( C ) INDIVIDUAL ISOLATE: PS201T6

( v i i ) IMMEDIATE SOURCE:
        ( A ) LIBRARY: LambdaGem (TM)-11 library of Kenneth E. Narva
        ( B ) CLONE: 201T635

( x i ) SEQUENCE DESCRIPTION: SEQ ID NO:1:

```
ATGAAAGAGT  CAATTTACTA  CAATGAAGAA  AATGAAATAC  AAATTTCACA  AGGAAACTGT       60

TTCCCAGAAG  AATTAGGACA  TAATCCTTGG  AGACAACCTC  AATCCACAGC  AAGAGTTATT      120

TATTTAAAAG  TAAAAGATCC  TATTGATACT  ACTCAATTAT  TAGAAATAAC  AGAAATCGAA      180

AATCCCAATT  ATGTATTACA  AGCTATTCAA  CTAGCTGCTG  CCTTCCAAGA  TGCATTAGTA      240

CCAACTGAAA  CAGAATTTGG  AGAAGCCATT  AGATTAGTA   TGCCTAAAGG  ATTAGAAGTT      300

GCAAAAACTA  TTCAACCTAA  GGGTGCTGTT  GTTGCTTACA  CAGATCAAAC  TCTGTCACAA      360

AGCAACAACC  AAGTTAGTGT  TATGATTGAT  AGAGTTATTA  GTGTTTTAAA  AACTGTAATG      420

GGAGTAGCTC  TTAGTGGTTC  CATTATAACT  CAATTAACAG  CTGCTATCAC  TGATACTTTT      480

ACAAACCTTA  ATACACAAAA  AGATTCTGCT  TGGGTTTTTT  GGGGAAAAGA  AACTTCACAT      540

CAAACAAATT  ACACATATAA  TGTCATGTTT  GCAATTCAAA  ATGAAACAAC  TGGACGCGTA      600

ATGATGTGTG  TACCTATTGG  ATTTGAAATT  AGAGTATTTA  CTGATAAAAG  AACAGTTTTA      660

TTTTTAACAA  CTAAAGATTA  CGCTAATTAT  AGTGTGAATA  TTCAAACCCT  AAGGTTTGCT      720

CAACCACTTA  TTGATAGCAG  AGCACTTTCA  ATTAATGATT  TATCAGAAGC  ACTTAGATCT      780

TCTAAATATT  TATAC                                                          795
```

( 2 ) INFORMATION FOR SEQ ID NO:2:

(i) SEQUENCE CHARACTERISTICS:
    (A) LENGTH: 265 amino acids
    (B) TYPE: amino acid
    (C) STRANDEDNESS: single
    (D) TOPOLOGY: linear (ii) MOLECULE TYPE: protein (iii) HYPOTHETICAL: YES (iv) ANTI-SENSE: NO (vi) ORIGINAL SOURCE:
    (A) ORGANISM: Bacillus thuringiensis
    (B) STRAIN: neoleoensis
    (C) INDIVIDUAL ISOLATE: PS201T6

(vii) IMMEDIATE SOURCE:
    (A) LIBRARY: LambdaGem (TM)-11 Library of Kenneth E. Narva
    (B) CLONE: 201T635

(xi) SEQUENCE DESCRIPTION: SEQ ID NO:2:

```
Met Lys Glu Ser Ile Tyr Tyr Asn Glu Glu Asn Glu Ile Gln Ile Ser
 1               5                  10                  15

Gln Gly Asn Cys Phe Pro Glu Glu Leu Gly His Asn Pro Trp Arg Gln
                20                  25                  30

Pro Gln Ser Thr Ala Arg Val Ile Tyr Leu Lys Val Lys Asp Pro Ile
            35                  40                  45

Asp Thr Thr Gln Leu Leu Glu Ile Thr Glu Ile Glu Asn Pro Asn Tyr
        50                  55                  60

Val Leu Gln Ala Ile Gln Leu Ala Ala Ala Phe Gln Asp Ala Leu Val
65                  70                  75                  80

Pro Thr Glu Thr Glu Phe Gly Glu Ala Ile Arg Phe Ser Met Pro Lys
                85                  90                  95

Gly Leu Glu Val Ala Lys Thr Ile Gln Pro Lys Gly Ala Val Val Ala
                100                 105                 110

Tyr Thr Asp Gln Thr Leu Ser Gln Ser Asn Asn Gln Val Ser Val Met
            115                 120                 125

Ile Asp Arg Val Ile Ser Val Leu Lys Thr Val Met Gly Val Ala Leu
        130                 135                 140

Ser Gly Ser Ile Ile Thr Gln Leu Thr Ala Ala Ile Thr Asp Thr Phe
145                 150                 155                 160

Thr Asn Leu Asn Thr Gln Lys Asp Ser Ala Trp Val Phe Trp Gly Lys
                165                 170                 175

Glu Thr Ser His Gln Thr Asn Tyr Thr Tyr Asn Val Met Phe Ala Ile
            180                 185                 190

Gln Asn Glu Thr Thr Gly Arg Val Met Met Cys Val Pro Ile Gly Phe
        195                 200                 205

Glu Ile Arg Val Phe Thr Asp Lys Arg Thr Val Leu Phe Leu Thr Thr
    210                 215                 220

Lys Asp Tyr Ala Asn Tyr Ser Val Asn Ile Gln Thr Leu Arg Phe Ala
225                 230                 235                 240

Gln Pro Leu Ile Asp Ser Arg Ala Leu Ser Ile Asn Asp Leu Ser Glu
            245                 250                 255

Ala Leu Arg Ser Ser Lys Tyr Leu Tyr
            260                 265
```

(2) INFORMATION FOR SEQ ID NO:3:

(i) SEQUENCE CHARACTERISTICS:
    (A) LENGTH: 222 amino acids (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Bacillus thuringiensis
        (B) STRAIN: neoleoensis
        (C) INDIVIDUAL ISOLATE: PS201T6

(xi) SEQUENCE DESCRIPTION: SEQ ID NO:3:

```
Val Lys Asp Pro Ile Asp Thr Thr Gln Leu Leu Glu Ile Thr Glu Ile
1               5                   10                  15

Glu Asn Pro Asn Tyr Val Leu Gln Ala Ile Gln Leu Ala Ala Ala Phe
            20                  25                  30

Gln Asp Ala Leu Val Pro Thr Glu Thr Glu Phe Gly Glu Ala Ile Arg
        35                  40                  45

Phe Ser Met Pro Lys Gly Leu Glu Val Ala Lys Thr Ile Gln Pro Lys
    50                  55                      60

Gly Ala Val Val Ala Tyr Thr Asp Gln Thr Leu Ser Gln Ser Asn Asn
65                  70                  75                  80

Gln Val Ser Val Met Ile Asp Arg Val Ile Ser Val Leu Lys Thr Val
            85                  90                  95

Met Gly Val Ala Leu Ser Gly Ser Ile Ile Thr Gln Leu Thr Ala Ala
            100                 105                 110

Ile Thr Asp Thr Phe Thr Asn Leu Asn Thr Gln Lys Asp Ser Ala Trp
        115                 120                 125

Val Phe Trp Gly Lys Glu Thr Ser His Gln Thr Asn Tyr Thr Tyr Asn
    130                 135                 140

Val Met Phe Ala Ile Gln Asn Glu Thr Thr Gly Arg Val Met Met Cys
145                 150                 155                 160

Val Pro Ile Gly Phe Glu Ile Arg Val Phe Thr Asp Lys Arg Thr Val
                165                 170                 175

Leu Phe Leu Thr Thr Lys Asp Tyr Ala Asn Tyr Ser Val Asn Ile Gln
            180                 185                 190

Thr Leu Arg Phe Ala Gln Pro Leu Ile Asp Ser Arg Ala Leu Ser Ile
        195                 200                 205

Asn Asp Leu Ser Glu Ala Leu Arg Ser Ser Lys Tyr Leu Tyr
    210                 215                 220
```

CONTROLLING HEMIPTERAN INSECT PESTS WITH BACILLUS THURINGIENSIS ISOLATE PS123D1

CROSS-REFERENCE TO A RELATED APPLICATION

This application is a continuation-in-part of application Ser. No. 08/475,924, filed Jun. 7, 1995, issued as U.S. Pat. No. 5,723,440.

FIELD OF THE INVENTION

The present invention relates to methods for controlling insect pests of the order Hemiptera. In particular, δ-endotoxins of Bacillus thuringiensis (B.t.) have been discovered, unexpectedly, to control hemipteran insect pests, e.g. Lygus hesperus.

BACKGROUND OF THE INVENTION

The soil microbe Bacillus thuringiensis (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–S7). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of B. thuringiensis var. kurstaki have been used for many years as commercial insecticides for lepidopteran pests. For example, B. thuringiensis var. kurstaki HD-1 produces δ-endotoxin crystals which are toxic to the larvae of a number of lepidopteran insects.

In recent years, however, investigators have discovered B.t. pesticides with specificities for a much broader range of pests. For example, other species of B.t., namely B.t. var. israelensis and B.t. var. tenebrionis (a.k.a. M-7, a.k.a. B.t. var. san diego), have been used commercially to control insects of the orders Diptera and Coleoptera, respectively (Gaertner, F. H. [1989] "Cellular Delivery Systems for Insecticidal Proteins: Living and Non-Living Microorganisms," in Controlled Delivery of Crop Protection Agents, R. M. Wilkins, ed., Taylor and Francis, New York and London, 1990, pp. 245–255). See also Couch, T. L. (1980) "Mosquito Pathogenicity of Bacillus thuringiensis var. israelensis," Developments in Industrial Microbiology 22:61–76; and Beegle, C. C., (1978) "Use of Entomogenous Bacteria in Agroecosystems," Developments in Industrial Microbiology 20:97–104. Krieg et al. Krieg, A., A. M. Huger, G. A. Langenbruch, W. Schnetter [1983] Z. ang. Ent. 96:500–508), describe Bacillus thuringiensis var. tenebrionis, which is reportedly active against two beetles in the order Coleoptera. These are the Colorado potato beetle, Leptinotarsa decemlineata, and the beetle Agelastica alni.

Recently, new subspecies of B.t. have been identified, and genes responsible for active δ-endotoxin proteins have been isolated (Höfte, H., H. R. Whiteley [1989] Microbiological Reviews 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al. (Prefontaine, G., P. Fast, P. C. K Lau, M. A. Hefford, Z. Hanna, R. Brosseau [1987] Appl. Environ. Microbiol. 53(12):2808–2814) describe probes useful in classifying lepidopteran-active genes. The discovery of strains specifically toxic to other pests has been reported (Feitelson, J. S., J. Payne, L. Kim [1992] Bio/Technology 10:271–275). B.t. crystalline toxins are generally recognized as being protoxins, requiring either particular physicochemical conditions (ie., pH, redox, ionic strength), or the action of certain proteases, or both, to generate an active toxin (Höfte and Whiteley, supra). In most cases, the insect supplies conditions for activation of the toxin; however, cases have been documented where pre-solubilization or pre-proteolysis have been necessary for optimum activity (Jacquet, J., R. Hutter, P. Luthy [1987] "Specificity of Bacillus thuringiensis delta-endotoxin," Appl. Environ. Microbiol. 53:500–504) or detection of activity (Lambert, B., H. R. Höfte, K. Annys, S. Jansens, P. Soetaert, M. Peferoen [1992] "Novel Bacillus thuringiensis insecticidal crystal protein with a silent activity against coleopteran larvae," Appl. Environ. MicrobioL 58:2536–2542).

The cloning and expression of a B.t. crystal protein gene in Escherichia coli has been described in the published literature (Schnepf, H. E., H. R. Whiteley [1981] Proc. Natl. Acad. Sci. U.S.A. 78:2893–2897). U.S. Pat. No. 4,448,885 and U.S. Pat. No. 4,467,036 both disclose the expression of B.t. crystal proteins in E. coli. U.S. Pat. Nos. 4,797,276 and 4,853,331 disclose B. thuringiensis var. tenebrionis (a.k.a. B.t. san diego, a.k.a. M-7) which can be used to control coleopteran pests in various environments. U.S. Pat. No. 4,918,006 discloses Bacillus thuringiensis var. israelensis toxins which are active against dipteran pests and reports that a protein of about 27 kDa, and fragments thereof, are responsible for the dipteran activity. U.S. Pat. No. 4,849,217 discloses B.t. isolates which have activity against the alfalfa weevil. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Hemiptera represent a major group of insects that have not, to date, been effectively controlled by B.t. δ-endotoxins. Numerous hemipteran pest species, most notably Lygus species, cause considerable plant damage and economic loss each year.

Hemiptera ranks among the most economically destructive orders. See Arnett, R. H. Jr. ([1985] American Insects, Van Nostrand Reinhold Co., Inc., New York). Of all Hemiptera, the mirids (Hemiptera: Miridae; includes Lygus) are the most notorious crop pests. Feeding causes injury that weakens plants and is a mode of plant disease transmission. In addition to L. hesperus, other pest Lygus include: L. lineolaris (Beauv.), L. pratensis (L.), L. rugulipennis Popp., and the common green capsid (Lygus pabulinus (L.)). Members of this genus are found variously on cotton, potato, sugar beet, celery, beans, peach, apple, alfalfa, pear, plum, quince and a variety of nursery stock, ornamental plants and vegetable crops. Specific Mirid pests include: the potato capsid Calocoris norvegicus (Gmel.), a pest of potato and brassicas (e.g., cabbage, cauliflower, broccoli, kale, Brussels sprout, turnip); the stack bug (also carrot plant bug) *Orthops campestris* (L.), a pest of carrot, celery, parsnip, parsley and dill; the apple capsid *Plesiocoris rugicollis* (Fall.), a pest of apple, currants and gooseberry; the tomato bug *Cyrtopeltis modestus* (Distant), a pest of tomatoes; the suckfly *Cyrtopeltis notatus* (Distant), a pest of tobacco; the white marked fleahopper *Spanagonicus albofasciatus* (Reuter), injurious to grass, with damage particularly noticeable on golf greens; the honeylocust plant bug *Diaphnocors chlorionis* (Say), a pest of beets; the onion plant bug *Labopidicola allii* Knight, a pest of cultivated and wild onions; the cotton fleahopper *Pseudatomoscelis seriatus* (Reuter), found on cotton; the rapid plant bug *Adelphocoris rapidus* (Say), an occasional pest of cotton and legumes; the four-lined plant bug *Poecilocapsus lineatus* (Fabricius), often a pest of garden crops.

Other Hemipteran pests include:

Lygaeidae (seed bug family): chinch bug (*Blissus leucopterus* (Say)) is a pest of maize, sorghums, wheat, millets, rice, barley, rye and oats; false chinch bugs (*Nysius* spp., e.g., *N. ericae, N. raphanus* Howard) are pests of brassicas, beets and potato.

Pentatomidae (stink bug family): the brown stink bug, *Euschistus servus* (Say) is a pest of cotton. The green stink bug, *Nezara viridula* (L.) is a generalist pest of seedlings, especially vegetables and legumes; Eurygaster species, e.g. *E. austiaca* (Schr.) and *E. integriceps* (Put.) (wheat shield bug, Sunn pest, Senn bug) attack wheat and barley.

Coreidae (squash bug family): *Anasa tristis* (DeGreer) (squash bug) is a local pest of squash; *A. armigera* (Say) (homed squash bug) is an occasional pest of cultivated cucumber.

Pyrrhocoridae (red bug and cotton stainer family): the cotton stainer *Dysdercus suturellus* (Herrich-Schaeffer) is a pest of cotton.

Tingidae (lace bug family): *Corythucha arcuata* (Say) often is a pest of roses, maple, apple and chestnut. Other Corythucha species include the cotton lace bug, chrysanthemum lace bug, elm lace bug and hawthorn lace bug.

Belostomatidae (giant water bug family): members of this family are known to attack and suck the blood of fishes and therefore can be a pest in fish hatcheries.

Members of the Reduviidae and Cimicidae (including kissing bug and bed bugs, respectively) bite mammals and transmit diseases contractible by humans.

The digestive system of hemipterans is unusual among the insects in several ways: certain hydrolytic digestive enzymes are absent such as trypsin; the midgut lacks a peritrophic membrane, and there is no crop. These features reflect the liquid diet and sucking mode of feeding, subject to evolutionary constraints. Because of the differences in diet, feeding mode, and digestive physiology and biochemistry, one would not necessarily expect that proteins having insecticidal activity against leaf-chewing insects would also have activity against fluid-feeding Hemiptera.

*Bacillus thuringiensis* PS201T6, NRRL B-18750, deposited on Jan. 9, 1991, or a δ-endotoxin therefrom, was previously found to have activity against certain pests. For example, see U.S. Pat. Nos. 5,273,746; 5,298,245; and 5,302,387, which disclose the use of *B.t.* PS201T6. *B.t.* isolates PS123D1 has been disclosed in EP 0 409 438. *B.t.* isolate PS71M3 has been disclosed in EP 0 626 809 and in U.S. Pat. No. 5,273,746. The above patents do not disclose or suggest the use of any *B.t.* isolate to control hemipteran insect pests.

Practice of the present invention provides an alternative to control of hemipteran pests with chemical pesticides, thereby allowing more environmentally-friendly insect management and providing a tool for management of insecticide resistance.

BRIEF SUMMARY OF THE INVENTION

The subject invention concerns the use of *Bacillus thuringiensis* (*B.t.*) δ-endotoxins to control hemipteran insect pests. Specifically exemplified herein is the use of the *B.t.* isolate PS201T6 and toxins therefrom to control the hemipteran insect pest *Lygus hesperus*. The use of *B.t.* var. *israelensis* isolates and toxins is also described.

The subject invention also includes the use of variants of the exemplified *B.t.* isolates and toxins which have substantially the same pesticidal properties as the exemplified isolates and toxins. These variants include mutant microbes. Procedures for making mutants are well known in the microbiological art. Ultraviolet light and chemical mutagens such as nitrosoguanidine are used extensively toward this end.

Recombinant hosts which have been transformed to express *B.t.* toxins can also be used according to the subject invention. These recombinant hosts may be, for example, microorganisms or plants.

According to the subject invention, hemipteran insect pests can be controlled using the *B.t.* isolate itself, variants of the *B.t.* isolates, δ-endotoxins obtained from said isolates, commercial preparations made from cultures of the isolates, or toxins produced by DNA of this isolate. In one embodiment, the toxins may be produced by DNA which has been transformed into another host. In a preferred embodiment, the transformed host is a plant.

BRIEF DESCRIPTION OF THE SEQUENCES

SEQ ID NO.1 is the nucleotide sequence encoding an approximately 30 kDa toxin of PS201T6.

SEQ ID NO.2 is the deduced amino acid sequence of an approximately 30 kDa toxin of PS201T6.

SEQ ID NO.3 is the amino acid sequence of a truncated 201T6 toxin of about 25 kDa.

DETAILED DISCLOSURE OF THE INVENTION

The subject invention concerns the discovery of a new method for controlling hemipteran insect pests which involves contacting said pests with a *Bacillus thuringiensis* (*B.t.*) δ-endotoxin in a manner wherein the hemipteran insect ingests the δ-endotoxin. Specifically exemplified is the use of toxins from the *B.t.* isolate known as PS201T6. Also exemplified is the use of toxins from *Bacillus thuringiensis* var. *israelensis* (*B.t.i.*) isolates to control hemipteran pests.

The *Bacillus thuringiensis* isolate PS201T6 has the following characteristics in its biologically pure form and as compared to *B.t.* HD-1:

TABLE 1

| Comparison of *B.t.* PS201T6, and *B.t.* HD-1 | | |
|---|---|---|
| | *B.t.* PS201T6 | *B.t.* HD-1 |
| Inclusions: | elliptical & bipyramid | bipyramid |

TABLE 1-continued

Comparison of B.t. PS201T6, and B.t. HD-1

|  | B.t. PS201T6 | B.t. HD-1 |
|---|---|---|
| Approximate molecular wt. of proteins by SDS-PAGE | 133,000 31,000 | 130,000 68,000 |
| Host range | Cockroaches Diptera Corn Rootworm | Lepidoptera |

The *israelensis* variety of *B.t.* is well known and readily recognized by those skilled in this art. Characteristics generally associated with the *israelensis* category of *B.t.* include dipteran activity, H14 serotype, and a protein pattern which includes an approximately 28 to 33 kD protein and, generally, additional proteins of about 70 kD and 130 kD. Other *B.t.* varieties which express *israelensis* -type toxins can also be used according to the subject invention. Such toxins would have a size similar to the toxins produced by *B.t.i.* and a similar activity profile, including dipteran activity. *B.t.* var. *morrisoni* serotype 8a, 8b have, for example, been reported to express *B.t.i.*-type toxins. An example of such an isolate is PS71M3. As used herein, the term "*Bacillus thuringiensis* var. *israelensis* toxin" includes toxins which are similar or related to toxins expressed by *B.t.i.* but which happen to be expressed by a different variety of *B.t.*

The isolate designated PS123D1 is specifically exemplified as a *B.t.i.* isolate useful according to the subject invention. Of particular interest in controlling hemipteran pests are toxins of approximately 28 to 33 kD of a *B.t.i.* isolate or, preferably, modified forms of this toxin. One embodiment of the subject invention involves the use of truncated forms of the 28 kDa PS123D1 toxin to control hemipterans. A specific example is the truncated toxin which has amino acids removed from the N-terminus and is about 25 kDa. As described herein, the truncated forms of the toxins can be obtained through treatment of *B.t.* culture supernatants and/ or by growing *B.t.* cultures under appropriate conditions to result in the production of activated toxins as a result of the advantageous effects of endogenous proteases. Other modifications which cause, for example, solubilization of the *B.t.i.* toxin can also be utilized to obtain highly active toxins.

The *Bacillus thuringiensis* isolate PS123D1 has the following characteristics in its biologically pure form:

TABLE 2

Characteristics of B.t. PS123D1

|  | B.t. PS123D1 |
|---|---|
| Inclusions: | amorphic |
| Approximate molecular wt. of proteins by SDS-PAGE | 133,000 127,000 72,000 28,000 |

The cultures disclosed in this application have been deposited in the Agricultural Research Service Pat. Culture Collection (NRRL), Northern Regional Research Center, 1815 North University Street, Peoria, Ill. 61604, U.S.A.

| Culture | Repository No. | Deposit date |
|---|---|---|
| Bacillus thuringiensis PS201T6 | NRRL B-18750 | January 9, 1991 |
| E. coli NM522 (pMYC2362) | NRRL B-21018 | December 2, 1992 |
| E. coli NM522 (pMYC2357) | NRRL B-21017 | December 2, 1992 |
| Bacillus thuringiensis PS123D1 | NRRL B-21011 | October 13, 1992 |
| Bacillus thuringiensis PS71M3 | NRRL B-18930 | December 27, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

In one preferred embodiment of the subject invention, a toxin from *B.t.* isolate PS201T6 is used to achieve control of hemipteran insect pests. In another preferred embodiment, the PS201T6 toxin is activated. Toxins can be activated by, for example, culturing the microbe, under conditions which facilitate the activation of said toxin by the action of compounds which exist naturally or are produced in said culture. Activation may also be achieved by adding a compound to a *Bacillus thuringiensis* strain PS201T6 culture, or a supernatant thereof, wherein said compound participates in the activation of said toxin either through direct action on said toxin or by facilitating the action of a second compound. The additional compound may be, for example, a protease, or a compound which raises the pH of the culture or supernatant.

*Bacillus thuringiensis* PS201T6 is now available to the public, without restriction, by virtue of the issuance of U.S. Pat. No. 5,273,746. Plasmid pMYC2362 harbors a gene encoding a 130 kDa toxin from PS201T6. Plasmid pMYC2357 harbors a gene encoding a 30 kDa toxin from PS201T6. Further information regarding examples of cloning genes from PS201T6 can be found in EP-A-0 708 830 and WO 95/02694. Further examples of cloning genes from PS71M3 are described in WO 95/02694 and EP-A-0 457 498.

Genes and toxins. In one embodiment of the subject invention, genes which encode *B.t.* toxins active against hemipteran insect pests are used to transform a suitable host. The genes and toxins useful according to the subject invention include not only the full length sequences but also fragments of these sequences, variants, mutants, and fusion proteins which retain the characteristic pesticidal activity of the toxins specifically exemplified. As used herein, the terms "variants" or "variations" of genes refer to nucleotide sequences which encode the same toxins or which encode equivalent toxins having similar pesticidal activity. As used herein, the term "equivalent toxins" refers to toxins having the same or essentially the same biological activity against the target pests as the claimed toxins.

It would be apparent to a person skilled in this art, having the benefit of this disclosure, that genes encoding hemipteran-active toxins can be identified and obtained through several means. The genes can be obtained from the isolate deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from $B.t.$ isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other $B.t.$ toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect the pesticidal activity of the protein.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Recombinant hosts. The toxin-encoding genes harbored by the isolates disclosed herein can be introduced into a wide variety of microbial or plant hosts. Expression of the toxin gene results, directly or indirectly, in the production of the toxin. With suitable microbial hosts, e.g., Pseudomonas, the microbes can be applied to the situs of the pest, where they will proliferate and be ingested by the pest, resulting in control of the pest. Alternatively, the microbe hosting the toxin gene can be treated under conditions that prolong the activity of the toxin and stabilize the cell. The treated cell, which retains the toxic activity, then can be applied to the environment of the target pest. Methods for treatment of microbial cells are disclosed in U.S. Pat. Nos. 4,695,455 and 4,695,462, which are incorporated herein by reference.

A wide variety of ways are available for introducing a $B.t.$ gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Furthermore, materials and methods for introducing $B.t.$ genes into plants in order to confer upon such plants the ability to produce insecticidal toxins are well known in the art. In a preferred embodiment, the $B.t.$ genes are modified to facilitate optimal stability and expression in the selected plant host. In this regard, U.S. Pat. No. 5,380,831 is incorporated herein by reference.

Mutants. Mutants of the isolate described herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

Following are examples which illustrate procedures for practicing the present invention. These examples should not be construed as limiting. All percentages are by weight and all solvent mixture proportions are by volume unless otherwise noted.

EXAMPLE 1

Culturing $B.t.$ Strain PS201T6

A subculture of $B.t.$ isolate strain PS201T6 can be used to inoculate the following peptone, glucose, and salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2
Production of Activated 201T6 Toxin (201T6-D)

Activated 201T6 toxin can be produced by a variety of methods which result in truncation of the 201T6 toxin. In this regard, reference can be made to WO95/02693. In one such method, cultures of PS201T6 were harvested by centrifugation and resuspended to 1/9th to 1/25th of their original culture volume in 0.1 $Na_2CO_3/NaHCO_3$ pH 11.0 containing 0.5 mg/ml pronase E (Sigma Chemical Company, P-5147 Type XIV bacterial protease from *Streptomyces griseus*). The suspension was incubated at 37° C. overnight with mixing. The suspensions were dialyzed against 2 changes of 50 to 100 volumes each of either distilled water or 0.1M $Na_2CO_3/NaHCO_3$ pH 9.5 to yield "dialyzed suspensions."

The suspension resulting from 0.1M $Na_2CO_3/NaHCO_3$ pH 9.5 dialysis was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant."

Dried preparations of the processed toxin were prepared either before or after filtration by dialyzing against 2 changes of 50 to 100 volumes distilled water, followed by lyophilization (lyophilized, pronase-treated toxin).

EXAMPLE 3
Alternative Method for Production of Activated 201T6 Toxin

Cultures of PS201T6 were harvested by centrifugation and resuspended to 1/9th to 1/25th of their original culture volume in 0.1M $Na_2CO_3/NaHCO_3$, 0.5% 2-mercaptoethanol, pH 11.0. The suspension was incubated for about 2 hours at room temperature. The suspension was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant." The suspensions were dialyzed against 2 changes of 50 to 100 volumes each of either distilled water or 0.1M $Na_2CO_3/NaHCO_3$ pH 9.5 to yield "dialyzed suspensions."

Dried preparations of the processed toxin were prepared either before or after filtration by dialyzing against two changes of 50 to 100 volumes distilled water, followed by lyophilization. Material prepared according to this procedure is referred to herein as 201T6-D.

EXAMPLE 4
Activity of *B.t.* Isolates Against the Hemipteran Insect *Lygus hesperus*

Five newly-emerged ($\leq$one week old) *L. hesperus* adults were placed in a 1.0 oz. plastic portion cup (Fabrikal Corp.) with two pinholes in the side to allow gas exchange. A small piece of Scott MICROWIPES tissue was placed in the bottom of the cup to absorb liquid excreta. In place of a lid, two pieces of PARAFILM were stretched across the top, sandwiching in between them 200 $\mu$L of test solution. "Autoprocessed" *B.t.* PS201T6 cell culture broth (activated by resident proteases as described in Example 3) was presented to *L. hesperus* adults. The autoprocessed broth was estimated to contain approximately 4.5 mg/ml of toxin. 1 ml of the broth was diluted to 100 ml with a 15% sucrose solution. 200 $\mu$l of the resulting 45 $\mu$g/ml solution was used as the test solution. Insects were allowed to feed for three days. Mortality after three days was compared with that of starved insects and control insects provided a "blank" of 15% sucrose solution that contained no toxin. After establishing activity of 45 $\mu$g/mL *B.t.* PS201T6 after three days, a subsequent experiment was conducted to establish activity of 4.5 $\mu$g/mL after two days. Representative results are shown in Tables 3 and 4.

TABLE 3

Three-day mortality of *Lygus hesperus* provided 45 $\mu$g *B.t.* PS201T6/mL

| Treatment | Initial number of live insects | Number of insects dead after 3 days | Percent of insects dead after 3 days |
|---|---|---|---|
| 15% sucrose solution | 25 | 7 | 28 |
| 45 $\mu$g B.t. PS201T6/mL of 15% sucrose solution | 25 | 17 | 68 |
| Starved (no food, water) | 25 | 25 | 100 |

TABLE 4

Two-day mortality of *Lygus hesperus* provided 4.5 $\mu$g *B.t.* PS201T6/mL

| Treatment | Initial number of live insects | Number of insects dead after 2 days | Percent of insects dead after 2 days |
|---|---|---|---|
| 15% sucrose solution | 50 | 29 | 58 |
| 4.5 $\mu$g B.t. PS201T6/mL of 15% sucrose solution | 50 | 41 | 82 |
| Starved (no food, water) | 50 | 50 | 100 |

EXAMPLE 5
Activity of *B.t.* Isolate PS201T6 Against the Hemipteran Insect *Lygus lineolaris*

As an alternative to the filter paper bioassay method, an insect is presented with "SCOTCH BRITE" or similar material saturated with the test mixture. The "SCOTCH BRITE" mesh material is cut from BioRad "MINITRANSBLOT" cell fiber pads (8×11 cm) into cubes approximately 0.5 cm per side. The cubes are then saturated with test solution and a single cube is placed into a 1.25 oz "SOLO" Cup Company plastic souffle cup along with one *L. lineolaris* adult. The container is sealed with a souffle cup lid, and several pinholes are made in the cup or lid to provide adequate air exchange. The insect is allowed to feed ad libitum, and mortality is measured after four days.

Test solutions were prepared by feeding protein samples or blanks with sterile-filtered (0.2 $\mu$m) sucrose solution in amounts needed to obtain desired protein concentrations and 10% sucrose in the final test solution. Proteins can be obtained as described in Example 3. Prior to sterile-filtering the sucrose solution, green food-grade vegetable dye (Iris Co.) was added to provide a visual stimulus to encourage feeding. Feeding was readily observed; within minutes of presentation with a cube containing dyed test solution, insects could be seen inserting the stylet into the cube mesh. Dyed excreta was visible shortly thereafter, generally within minutes of initiation of feeding. Results are shown in Table 5. Dose is expressed as µg toxin/mL diet. A buffer blank control and a BSA control were used as the negative controls. The buffer blank was run at a concentration equivalent to the background in the 1000 µg/mL treatment. The BSA control was run at 500 µg BSA/mL diet.

TABLE 5

Summary of mortality data (including summation across buffer and BSA negative controls)

| Dose | Number dead/total | Percentage dead |
| --- | --- | --- |
| 0 (controls) | 21/240 | 9 |
| 500 | 60/119 | 50 |
| 1000 | 62/90 | 69 |

EXAMPLE 6

Activated Toxins from *B.t.i.*

The removal of a portion of the N-terminus of the 123D1 28 kDa toxin results in an advantageous activation of this toxin which increases the potency of its activity. Removal of amino acids can be accomplished by treatment with trypsin or other appropriate enzyme, or enzyme mixture, such as pronase or endogenous proteins in *B.t.* culture broths. Other biologically active fragments could be obtained by those skilled in the art using the teachings provided herein.

As those skilled in the art having the benefit of this disclosure would readily recognize, the specific media used to grow the *B.t.* culture can be modified to achieve optimum activation of the *B.t.* toxin. For example, the cell density can be modulated by adjusting or changing the culture medium. Also, media having proteases therein can be used to enhance the activation of the *B.t.* toxins.

EXAMPLE 7

Insertion of Toxin Genes Into Plants

One aspect of the subject invention is the transformation of plants with genes encoding a toxin active against hemipteran pests. The transformed plants are resistant to attack by hemipterans.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al (1985) EMBO J. 4:277–287.

Once the insertestable there and, as a ed in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterum tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic *B.t.* genes for use in plants are known in the art.

EXAMPLE 8
Cloning of Novel *B.t.* Genes Into Insect Viruses

A number of viruses are known to infect insects. These viruses include, for example, baculoviruses and entomopoxviruses. In one embodiment of the subject invention, hemipteran-active genes, as described herein, can be placed within the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of killing hemipteran insect pests which comprises administering to said pests, or the environment of said pests, a pesticidally effective amount of a *Bacillus thuringiensis* δ-endotoxin from the *Bacillus thuringiensis* isolate PS123D1.

2. The method according to claim 1, wherein the *Bacillus thuringiensis* δ-endotoxin is a full length toxin, or a hemipteran-killing fragment thereof.

3. The method according to claim 1, wherein said hemipteran insect pests are *Lygus hesperus*.

4. The method according to claim 1, wherein said hemipteran insect pests are *Lygus lineolaris*.

* * * * *

UNITED STATES PATENT AND TRADEMARK OFFICE
CERTIFICATE OF CORRECTION

PATENT NO. : 5,885,963

DATED : March 23, 1999

INVENTOR(S) : Brian Stockhoff, Christopher Conlan

It is certified that error appears in the above-identified patent and that said Letters Patent is hereby corrected as shown below:

Column 2, line 7: "P.C.K Lau" should read --P.C.K. Lau--; and line 26: "*MicrobioL*" should read --*Microbiol.*--.

Column 3, line 10: "*Diaphnocors*" should read --*Diaphnocoris*--;

line 27: "*E. austiaca*" should read --*E. austriaca*--; and line 31: "(homed" should read --(horned--.

Column 12, line 7: "An et al" should read --An *et al.*--;

line 9: "Once the insertestable there and, as a ed in the genome," should read --Once the inserted DNA has been integrated in the genome,--; and line 20: "*Agrobacterum*" should read --*Agrobacterium*--.

UNITED STATES PATENT AND TRADEMARK OFFICE
CERTIFICATE OF CORRECTION

PATENT NO. : 5,885,963

DATED : March 23, 1999

INVENTOR(S) : Brian Stockhoff, Christopher Conlan

It is certified that error appears in the above-identified patent and that said Letters Patent is hereby corrected as shown below:

Column 17, line 58: "*thuringiensis*δ-endotoxin" should read

--*thuringiensis* δ-endotoxin--.

Signed and Sealed this

Ninth Day of November, 1999

Attest:

Q. TODD DICKINSON

*Attesting Officer*    *Acting Commissioner of Patents and Trademarks*